United States Patent [19]
Hasegawa et al.

[11] Patent Number: 5,441,962
[45] Date of Patent: Aug. 15, 1995

[54] METHOD FOR TREATING HYPERLIPEMIA

[75] Inventors: Motoharu Hasegawa; Kohji Shirai; Kiyohiko Matsumoto; Yasuhiko Suzuki; Isao Takahasi; Yuuiti Takarada; Mitsuyo Saito; Kumiko Yamamoto; Yositaka Takayama; Tsutomu Komazawa, all of Tokyo; Toshiji Sugai, Ohi, all of Japan

[73] Assignee: Nisshin Flour Milling Co., Ltd., Tokyo, Japan

[21] Appl. No.: 272,743

[22] Filed: Jul. 11, 1994

Related U.S. Application Data

[62] Division of Ser. No. 132,972, Oct. 7, 1993, abandoned.

[30] Foreign Application Priority Data

Oct. 9, 1992 [JP] Japan ................... 4-271480

[51] Int. Cl.⁶ ............................................. A61K 31/47
[52] U.S. Cl. ................................................. 514/309
[58] Field of Search ....................................... 514/309

[56] References Cited

U.S. PATENT DOCUMENTS 4,129,565 12/1978 Fukushima et al. ............... 546/142
4,517,365 5/1985 Koyama et al. .................... 546/142
4,666,919 5/1987 Ueno et al. ......................... 514/309
5,061,714 10/1991 Tadokoro et al. .................. 514/309
5,252,583 10/1993 Tadokoro et al. .................. 514/309

Primary Examiner—Marianne M. Cintins
Assistant Examiner—K. Weddington
Attorney, Agent, or Firm—Oblon, Spivak, McClelland, Maier & Neustadt

[57] ABSTRACT

The use of isoquinolinone derivatives as an antiarteriosclerosis agent and antihyperlipoproteinemics. The derivatives are of the formula

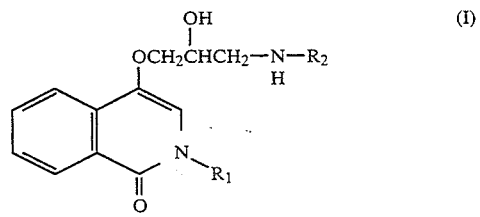

wherein $R_1$ is hydrogen or a $C_1-C_6$ alkyl group and $R_2$ is a $C_1-C_6$ alkyl group or the pharmaceutically acceptable salt thereof.

3 Claims, No Drawings

METHOD FOR TREATING HYPERLIPEMIA

This is a division, of application Ser. No. 08/132,972, filed on Oct. 7, 1993, abandoned.

FIELD OF THE INVENTION

This invention relates to the use of isoquinolinone derivatives for the treatment of arteriosclerosis and hyperlipemia. More particularly, the invention relates to an antiarteriosclerosis agent and antihyperlipoproteinemics which comprise an effective amount of those isoquinolinone derivatives or the pharmaceutically acceptable salts thereof.

BACKGROUND OF THE INVENTION

U.S. Pat. Nos. 4,129,565 and 4,517,365 disclose that the isoquinolinone derivatives of the formula

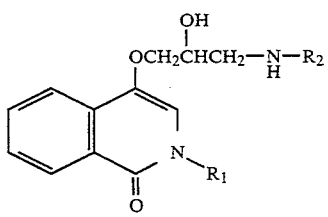

wherein $R_1$ is hydrogen or an alkyl group and $R_2$ is an alkyl group and the pharmaceutically acceptable salts thereof possess $\beta$-adrenergic blocking activity and are useful for the treatment of heart diseases such as hypertension, stenocardia and arrhythmia.

U.S. Pat. No. 5,061,714 also discloses that the isoquinolinone derivatives having the above formula are useful for the treatment of glaucoma or ocular hypertension.

However, there is no report on other pharmaceutical uses of those isoquinolinone derivatives.

DISCLOSURE OF THE INVENTION

In view of such situations, the present inventors have investigated other medical uses of the above-identified isoquinolinone derivatives and found that they possess potent anti-arteriosclerotic and anti-hyperlipemia activities and are useful for the treatment of arteriosclerosis and hyperlipemia.

Thus the present invention provides an antiarteriosclerosis agent and/or an antihyperlipoproteinemics which comprises as an active agent a compound of formula (I)

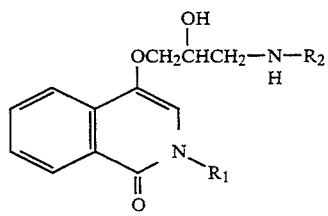

wherein $R_1$ is hydrogen or a $C_1-C_6$ alkyl group and $R_2$ is a $C^1-C_6$ alkyl group or the pharmaceutically acceptable salt thereof.

The invention also provides a method of treating an arteriosclerosis and/or a hyperlipemia which comprises administering an effective amount of said compound or the pharmaceutically acceptable salt thereof to a patient suffering from an arteriosclerosis and/or a hyperlipemia.

In the above formula (I), the $C_1-C_6$ alkyl group includes preferably straight or branched alkyl groups of 1-4 carbon atoms, e.g., methyl, ethyl, n-propyl, isopropyl, n-butyl isobutyl and tert.-butyl.

Representative examples of the compounds of formula (I) are illustrated below.

4-(3-tert.-Butylamino- 2-hydroxypropoxy)-1-isoquinolinone, 4-(3-tert.-Butylamino- 2-hydroxypropoxy)-2-methyl-1-isoquinolinone, 4-(3-Isopropylamino-2-hydroxypropoxy)-1-isoquinolinone, 4-(3-Isopropylamino-2-hydroxypropoxy)-2-methyl-1-isoquinolinone, 4-(3-Ethylamino-2-hydroxypropoxy)-1-isoquinolinone, 4-(3-Ethylamino-2-hydroxypropoxy)-2-methyl-1-isoquinolinone and 4-(3-Ethylamino-2-hydroxypropoxy)-2-ethyl-isoquinolinone.

The pharmaceutically acceptable salts include the salts of the isoquinolinone compounds with inorganic or organic acids such as hydrochloric, sulfuric, nitric, hydrobromic, oxalic, maleic, fumaric, citric, tartaric and malic acid.

When the isoquinolinone compounds of formula (I) or the pharmaceutically acceptable salts thereof are used as an antiarteriosclerosis agent and an antihyperlipoproteinemics, they can be formulated into pharmaceutical preparations in various dosage forms. Those preparations can be administered orally in the form of tablets, sugar-coated tablets, hard capsules, soft capsules or liquids such as solutions, emulsions or suspensions. Alternatively, the preparations may be administered parenterally in the form of injections.

The pharmaceutical preparations can be produced by known processes using additives well known in the art such as excipients, binders, diluents, stabilizers, preservatives, solubilizers, wetting agents, emulsifiers, lubricants, sweeteners, colorants, flavoring agents, buffers and antioxidants. Further, the pharmaceutical preparations of the isoquinolinone compounds with a stabilizing agent may be formed in such manner as described in U.S. Pat. No. 4,666,919 which is incorporated herein by reference.

For pharmaceutical preparations comprising the present compounds, the dose will vary depending on the manner of administration, the particular disease being treated and its severity, the overall health and condition of the patient, and the judgment of the prescribing physician, but generally a daily dose is orally 10 to 1200 mg for an adult.

Further, the present compounds have very low toxicity as shown in Example 2 described later.

The present invention will be further illustrated by the following examples.

EXAMPLE 1

In this example, the effects of the present compound on the wall of a blood vessel, a serum lipid and a blood glucose level were studied on the experimental sclerosis rabbits from the determination of the arterial sclerosis action, the assay of the components constituting the wall of the blood vessel and the transitional analysis of the damage of the blood wall with time.

Male Japanese white rabbits (25 months age) were randomly divided into three groups. A normal diet was given to one group (called hereafter "healthy group"). The remaining two groups were fed with 100 g/day of a high α-starch, high salinity and low protein, sclerosis diet containing 0.3% cholesterol (manufactured by Funabashi Farm), simultaneously injected intramuscularly with norepinephrine (3 mg) and bred for 150 days. One group of them was called hereafter "sclerosis group". To the remaining one group was orally administered at one dose per day a capsule which is filled with 3 mg of (±)-4-(3-tert.-butylamino-2-hydroxypropoxy)-2-methyl-1 (2H)-isoquinolinone hydrochloride, which group is called hereafter "drug administered group". Every 50 days, Aortic Pulse Wave Velocity (PWV) was measured to determine a average hardness of aorta of the rabbits. After five months and just before slaughter of the rabbits, blood was drawn to determine cholesterol in blood (T-Cho), triglyceride (TG), β-lipoprotein (β-Lp), HDL choresterol and a blood glucose level. After slaughter, a fifth intercostal pars in the thoracic aorta was extracted and then subjected to formalin fixation and embedding in paraffin. Subsequently, each component of smooth muscle cell (SMC), elastin (EL), collagen (CL), glycosaminoglycan (GAGs), PAS positive substance (PAS), calcium (Ca) and cholesterol (Cho) was histochemically observed and assayed.

The results are shown in the following tables.

TABLE 1

| | Δ PWV (m/sec) | | |
|---|---|---|---|
| | 0–50 days | 51–100 days | 101–150 days |
| Healthy group | 0.120 | 0.110 | 0.250 |
| Sclerosis group | −0.180 | 0.010 | 0.580 |
| Drug administered group | −0.110 | −0.290 | −0.890 |

TABLE 2

Proportion of Components Constituting the Wall of Aorta (% E)

| | Healthy group | Sclerosis group | Drug administered group |
|---|---|---|---|
| SMC | 48.01 | 37.98 | 46.72 |
| EL | 44.47 | 34.62 | 40.56 |
| CL | 34.26 | 28.26 | 30.33 |
| GAGs | 11.63 | 18.28 | 16.03 |
| PAS | 26.73 | 33.82 | 27.83 |
| Ca | 2.31 | 4.77 | 1.92 |
| Cho | 0.49 | 0.78 | 0.68 |

TABLE 3

Serum Lipid and Blood Glucose Level (mg/dl)

| | Healthy group | Sclerosis group | Drug administered group |
|---|---|---|---|
| T-Cho | 18.29 | 78.00 | 25.25 |
| TG | 79.43 | 130.67 | 65.40 |
| β-Lp | 9.00 | 23.83 | 2.75 |
| HDL-C | 9.00 | 18.33 | 15.44 |
| Blood glucose | 130.29 | 219.33 | 162.50 |

PWV is increasing with the advance of growth, maturation and ageing. Thus an increase in PWV value is an indication of arterial sclerosis (see Arterial Sclerosis, vol. 8, No. 1 April 1980, pp 91–95). Table 1 shows a change of PWV with time (ΔPWV) for each group, indicating that the PWV of the drug administered group was significantly improved in 150 days as compared with the sclerosis group. Table 2 shows that there was a remarkable improvement in arterial sclerosis.

EXAMPLE 2

4-(3-tert.-Butylamino- 2-hydroxypropoxy )-2-methyl-1-isoquinolinone hydrochloride and 4-(3-tert.-butylamino-2-hydroxypropoxy)-1-isoquinolinone hydrochloride, respectively were orally administered to male and female mice to determine the $LD_{50}$ value. The results are shown in Table 4.

TABLE 4

| Sex | $LD_{50}$ |
|---|---|
| Male | average 1393 mg/kg (1223–1587 mg/kg) |
| Female | average 1290 mg/kg (1063–1566 mg/kg) |

The following examples illustrate the pharmaceutical preparations of the present compounds.

| Preparation 1 - Tablets (one tablet) | |
|---|---|
| (±)-4-(3-tert.-Butylamino-2-hydroxypropoxy)-2-methyl-1(2H)-isoquinolinone hydrochloride | 20 mg |
| Magnesium silicate | 20 mg |
| Lactose | 98 mg |
| Hydroxypropylcellulose | 7.5 mg |
| Magnesium stearate | 1 mg |
| Hydrogenated vegetable oil | 3 mg |
| Total | 150 mg |

The above isoquinolinone compound, magnesium silicate and lactose were mixed and the mixture was kneaded with a solution of 5% hydroxypropyl cellulose in ethyl alcohol, followed by granulating the mixture to give granules of suitable particle sizes. These granules were dried and screened and then mixed with magnesium stearate and hydrogenated vegetable oil so that the granules were uniformly coated with the mixture of magnesium stearate and the oil. The granules were formulated by a rotary tableting machine into tablets each 7.0 mm in diameter, weighing 100 mg and having the hardness of 6 kg.

| Preparation 2 - Granules | |
|---|---|
| (±)-4-(3-tert.-Butylamino-2-hydroxypropoxy)-2-methyl-1(2H)-isoquinolinone hydrochloride | 10 mg |
| Magnesium oxide | 40 mg |
| Calcium hydrogenphosphate | 38 mg |
| Lactose | 10 mg |
| Hydroxypropylcellulose | 20 mg |

The above components except for hydroxypropylcellulose were mixed and the mixture was kneaded with a solution of 5% hydroxypropylcellulose in ethyl alcohol. The kneaded mixture was granulated by extrusion granulation. The granules were dried and screened to give the granules having particle size of 12–48 mesh.

| Preparation 3 - Syrups | |
|---|---|
| (±)-4-(3-tert.-Butylamino-2-hydroxypropoxy)-2-methyl-1(2H)-isoquinolinone hydrochloride | 1.000 g |
| Saccharose | 30.000 g |
| D-sorbitol 70 w/v % | 25.000 g |
| Ethyl paraoxybenzoate | 0.030 g |
| Propyl paraoxybenzoate | 0.015 g |
| Flavors | 0.200 g |
| Glycerin | 0.150 g |
| 96% Ethanol | 0.500 g |
| Distilled water | q.s. |

| Preparation 3 - Syrups | | |
| --- | --- | --- |
| | Total | 100 ml |

Saccharose, D-sorbitol, methyl paraoxybenzoate, propylparaoxybenzoate and the above isoquinolinone compound were dissolved in 60 g of warm water. After cooling, glycerin and a solution of the flavors in ethanol were added. To the mixture was then added water to make up 100 ml.

| Preparation 4 - Injections | |
| --- | --- |
| (±)-4-(3-tert.-Butylamino-2-hydroxypropoxy)-2-methyl-1(2H)-isoquinolinone hydrochloride | 10.0 mg |
| Sodium chloride | 81.0 mg |
| Sodium hydrogencarbonate | 8.40 mg |
| Distilled water for injection | q.s. |
| Total | 10.0 ml |

Sodium hydrogencarbonate, sodium chloride and the isoquinolinone compound were added to distilled water and dissolved therein to make up 10.0 ml.

| Preparation 5 - Suppositories | |
| --- | --- |
| (±)-4-(3-tert.-Butylamino-2-hydroxypropoxy)-2-methyl-1(2H)-isoquinolinone hydrochloride | 2 g |
| Polyethylene glycol 4000 | 20 g |

| Preparation 5 - Suppositories | |
| --- | --- |
| Glycerin | 78 g |
| Total | 100 g |

The isoquinolinone compound was dissolved in glycerin. To the solution was added polyethylene glycol 4000 and the mixture was warmed to a solution. The solution was poured into a suppository mold and solidified by cooling to prepare suppositories weighing 1.5 g per piece.

What is claimed is:

1. A method for treating a hyperlipemia which comprises administering to a patient suffering from hyperlipemia an effective amount of a compound of formula

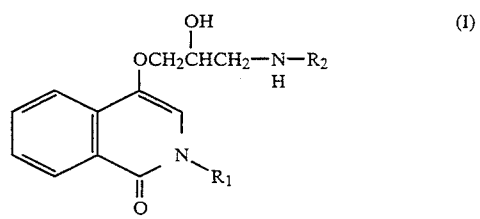

wherein $R_1$ is hydrogen or a $C_1$–$C_6$ alkyl group and $R_2$ is a $C_1$–$C_6$ alkyl group or the pharmaceutically acceptable salt thereof.

2. A method of claim 1 wherein $R_1$ is hydrogen and $R_2$ is a $C_1$–$C_4$ alkyl group.

3. A method of claim 1 wherein $R_1$ is a $C_1$–$C_4$ alkyl group and $R_2$ is a $C_1$–$C_4$ alkyl group.

* * * * *